(12) United States Patent
Koljonen

(10) Patent No.: US 6,681,037 B1
(45) Date of Patent: *Jan. 20, 2004

(54) APPARATUS FOR LOCATING FEATURES OF AN OBJECT USING VARIED ILLUMINATION

(75) Inventor: Juha Koljonen, Needham, MA (US)

(73) Assignee: Cognex Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/560,402

(22) Filed: Apr. 28, 2000

Related U.S. Application Data

(60) Provisional application No. 60/136,172, filed on May 27, 1999.

(51) Int. Cl.[7] .............................. G06K 9/00; H04N 7/18; G03B 15/02
(52) U.S. Cl. ....................... 382/141; 382/130; 382/145; 348/86; 348/125; 438/16; 362/3
(58) Field of Search .................................. 382/141–152, 382/130; 348/125–127, 86; 438/16; 29/833; 362/3–5, 11–13

(56) References Cited

U.S. PATENT DOCUMENTS

| | | | | |
|---|---|---|---|---|
| 5,761,336 A | * | 6/1998 | Xu et al. ..................... | 382/141 |
| 5,912,984 A | * | 6/1999 | Michael et al. ............. | 382/149 |
| 5,949,901 A | * | 9/1999 | Nichani et al. ............. | 382/149 |
| 5,982,927 A | * | 11/1999 | Koljonen ..................... | 382/168 |
| 6,134,342 A | * | 10/2000 | Doke et al. ................. | 382/141 |
| 6,163,374 A | * | 12/2000 | Otani et al. ............... | 356/152.1 |
| 6,259,827 B1 | * | 7/2001 | Nichani ....................... | 382/291 |
| 6,298,149 B1 | * | 10/2001 | Nichani et al. ............. | 382/149 |
| 6,317,513 B2 | * | 11/2001 | Michael et al. ............. | 382/145 |
| 6,445,812 B1 | * | 9/2002 | Lai et al. .................... | 382/141 |

* cited by examiner

Primary Examiner—Jayanti K. Patel
Assistant Examiner—Aaron Carter (AWC)

(57) ABSTRACT

An apparatus is provided for locating features of an object using varied lighting. The apparatus includes an image processor which is configured to send a plurality of commands to a digital camera which is used to obtain a plurality of digital images of an object without moving a location of the digital camera and the object. The image processor is arranged to receive the digital images of the object from the digital camera and the image processor is configured to control a level of illumination from at least one light source for illuminating the object. The image processor includes an illumination changer, a subtracter, an analyzer, and a controller to control and coordinate the illumination changer, the subtracter, and the analyzer. The illumination changer changes a level of illumination of any of the at least one lighting source before the image processor sends a command to the digital camera to obtain a next digital image. The subtracter subtracts at least a second digital image of the object from a first digital image of the object to produce a difference image of the object. The analyzer analyzes the difference image and locates at least one feature of the object based on the difference image.

32 Claims, 9 Drawing Sheets

APPARATUS FOR LOCATING FEATURES OF AN OBJECT USING VARIED ILLUMINATION

This application claims priority to U.S. provisional application No. 60/136,172, filed in the U.S. Patent and Trademark Office on May 27, 1999, the content of which is hereby incorporated by reference herein in its entirety.

BACKGROUND OF THE INVENTION

1. Field of the Invention

Aspects of the present invention relate to a machine vision apparatus for locating features on an object using varied illumination.

2. Description of Background Information

A vision tool exists that measures the area and location of solder paste printed on circuit boards for the purpose of inspecting the prints made for solder paste screen print machines. An apparatus compares a pre-print image of a circuit board at a given inspection site with a post-print image of the circuit board at the given inspection site to determine which pixels in the post-print image represent solder paste. The identified pixels are then grouped into regions and measured by a "blob" tool.

A main limitation of the above apparatus is that two images of each inspection site of each circuit board must be acquired—a before printing image and an after printing image. Moving the camera from inspection site to inspection site and visiting each site twice takes time and reduces the throughput of the apparatus.

SUMMARY

In an embodiment of the invention, an apparatus is provided for locating features of an object using varied lighting. The apparatus includes an image processor which is configured to send a plurality of commands to a digital camera which is used to obtain a plurality of digital images of an object without moving a location of the digital camera and the object. The image processor is arranged to receive the digital images of the object from the digital camera and the image processor is configured to control a level of illumination from at least one light source for illuminating the object. The image processor includes an illumination changer, a subtracter, an analyzer, and a controller to control and coordinate the illumination changer, the subtracter, and the analyzer. The illumination changer changes a level of illumination of any of the at least one lighting source before the image processor sends a command to the digital camera to obtain a next digital image. The subtracter subtracts at least a second digital image of the object from a first digital image of the object to produce a difference image of the object. The analyzer analyzes the difference image and locates at least one feature of the object based on the difference image.

BRIEF DESCRIPTION OF THE DRAWINGS

The above and other objects, features, and advantages of the present invention are further described in the Detailed Description which follows, with reference to the drawings by way of non-limiting exemplary embodiments of the invention, wherein.

DETAILED DESCRIPTION

Figure 1:
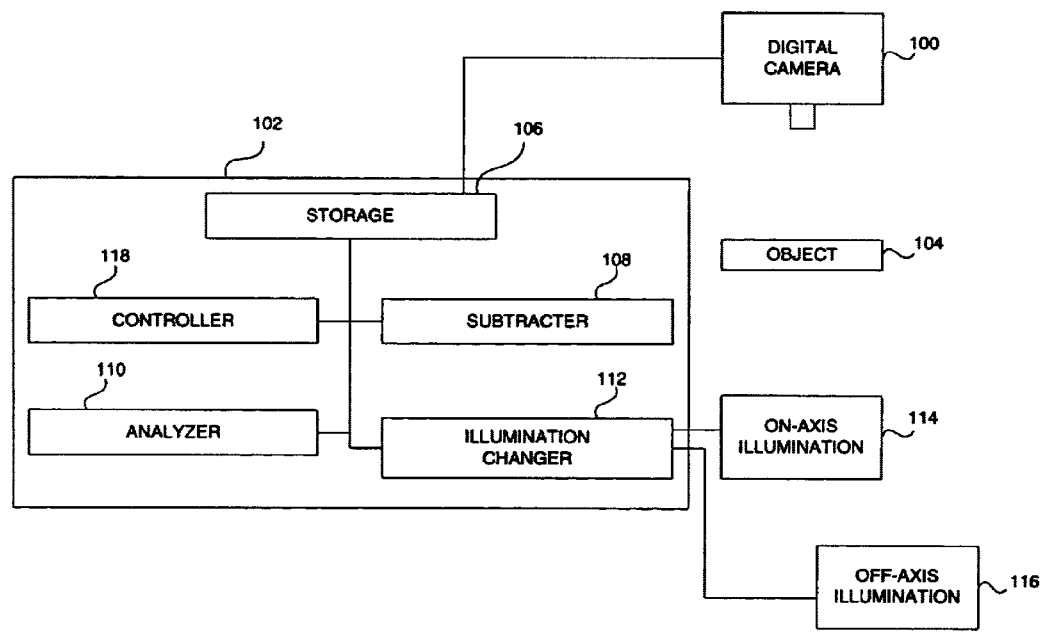
FIG. 1 is a diagram which illustrates the functional elements in an embodiment of the invention.

FIG. 1 illustrates a first embodiment of the invention. FIG. 1 shows a digital camera connected to an image processor 102. The digital camera 100 is arranged to acquire a digital image of object 104. The digital image is received by image processor 102 and stored in storage 106, which can be, for example, a computer memory.

A subtracter 108 receives a copy of the digital image from storage 106 and subtracts one of a copy of a digital image just received and a previously received digital image from another of the copy of the digital image just received with the previously received digital image to produce a difference image which is stored in storage 106. Analyzer 110 analyzes the difference image to locate at least one feature of the object based on the difference image.

Illumination changer 112 controls a level of illumination of at least one lighting source, for example, an on-axis illumination source 114 and an off-axis illumination source 116. The image processor adjusts a level of illumination of at least one of the illumination sources prior to sending commands to the digital camera to cause a digital image of the object to be acquired.

Controller 118 coordinates and controls the operation of the subtracter 108, the analyzer 110, and illumination changer 112. The controller 118 is, for example, a computer or a general purpose processor.

Figure 2:
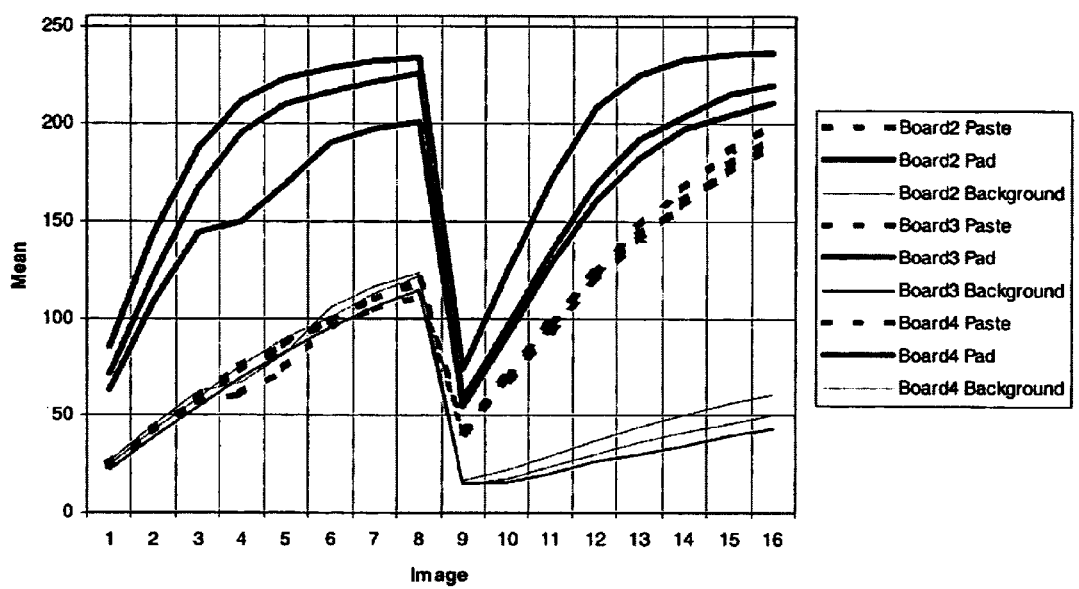
FIG. 2 is a chart showing a difference in light reflectivity properties of a printed circuit board, solder paste and background.

FIG. 2 illustrates how different regions on a printed circuit board respond differently to lighting changes. In particular, light reflects differently from a surface of solder paste than light reflecting from a surface of a circuit board or pads. Values one through 8 on a horizontal axis of FIG. 2 depict a lighting response of pads, paste, and boards to continually increasing on-axis illumination while holding off-axis illumination to zero. Values 9 through 16 on the horizontal axis of FIG. 2 depict a lighting response of pads, paste and boards to continually increasing off-axis illumination while holding the on-axis lighting at zero. The vertical axis represents the grey values of the pads, paste, or boards, where 9 is dark and 250 is light. Using these lighting conditions, the graph shows the light response of 300 random sample points taken from the same locations in different regions on three different circuit boards samples. For each type of material there are different trends of behavior for increasing illumination on-axis as opposed to increasing illumination off-axis.

For example, the pads change under both lighting conditions (increasing on-axis light and increasing off-axis light)

with a tendency to be brighter with on-axis lighting when observed from a vantage point of a camera. This occurs because pads are reflective, like mirrors, and will reflect on-axis light back into the camera. Off-axis light will be reflected at an incident angle away from the camera.

Similar to pads, the board reflects light less from increasing off-axis lighting than from on-axis lighting, such that the measured grey level of the board exposed to off-axis light is less than the measured grey level of the board exposed to similar intensity on-axis light. This occurs because the board has a flat surface like the pads. The surface is, however, less mirror-like and will reflect less light in general.

Lastly, the paste reflects light more from increasing off-axis lighting than increasing on-axis lighting. Among the board, pad and paste, only paste exhibits this behavior. This behavior occurs because of the texture quality of the paste which scatters light in all directions, such that some off-axis light is reflected into the camera. The different response of paste can be identified and used to detect paste on boards.

Figure 8:
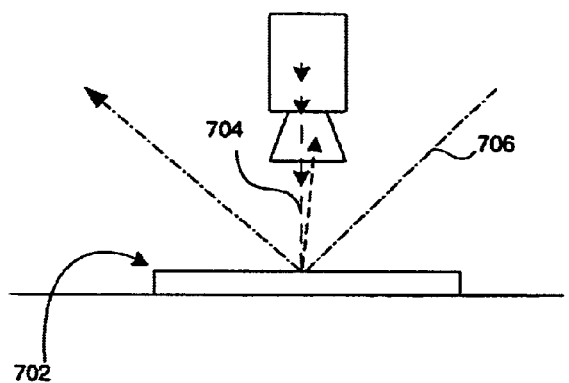
FIG. 8 illustrates light being reflected from a pad surface 702.

FIG. 8 illustrates light being reflected from a pad surface 702 As can be seen, most on-axis light 704 is reflected back into a camera 700. Off-axis light 706 is reflected elsewhere.

Figure 9:
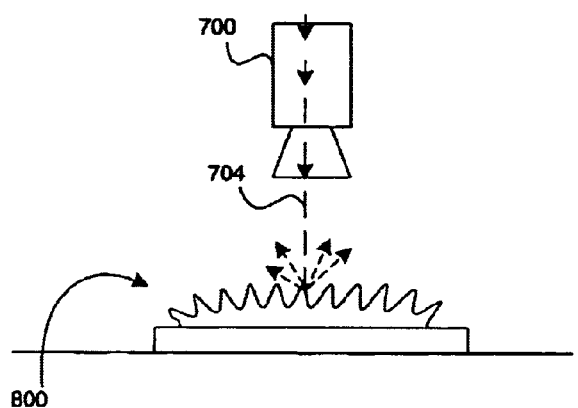
FIG. 9 illustrates light being reflected from a solder paste surface.

FIG. 9 illustrates light being reflected from a solder paste surface 800. On-axis light 704' is scattered due to the rough texture of the solder paste surface 800.

Figure 10:
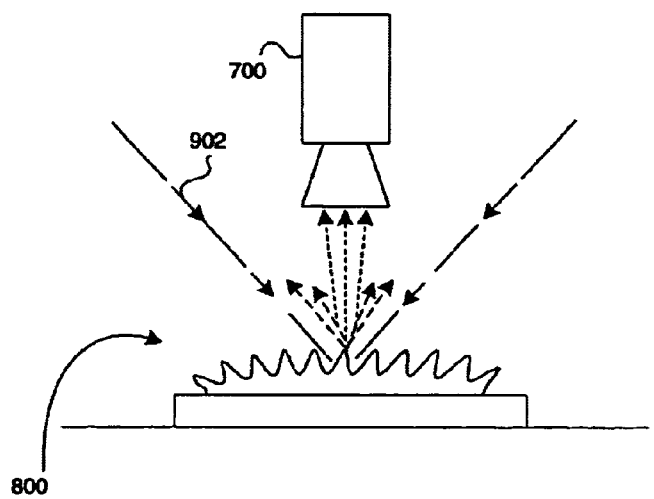
FIG. 10 is another view illustrating off-axis light being scattered due to a texture of the solder paste surface.

FIG. 10 illustrates off-axis light 902 being scattered due to the texture of the solder paste surface 800; however, off-axis light is illuminated from multiple sides, thus reflecting more light into the camera.

The above-mentioned behavior can be used to detect at least one feature of an object. For example, two or more images can be acquired, wherein each of the images have different off-axis and/or on-axis lighting. The two or more images are subtracted from one another to produce a difference image. Any locations in the difference image having a particular value, for example, a positive value, are deemed to represent paste. Any regions where the difference of two pixels as another particular value, for example, a negative value, are deemed to not represent paste. For instance, using an image of light illumination three and an image of lighting illumination 13, subtracting them, and evaluating the sign of the pixels in the difference image identifies paste from the remainder of the image.

Optionally, an embodiment of the invention recognizes and uses an additional trend of behavior for increasing illumination for each type of material—that is, the analyzer 110 analyzes a rate at which reflectivity increases.

As shown in FIG. 2, the paste has a steep slope in a region of continuously increasing off-axis illumination. That is, light reflecting from the paste due to off-axis lighting saturates the image quickly. The slope of the off-axis response is not only significant, it is also significantly greater than a rate of change of the reflectivity response of the paste in a region of increasing on-axis lighting. The board unlike the paste, has a small slope in a region of continuously increasing off-axis lighting. That is, off-axis lighting reflected from the board does not saturate the digital image quickly. The slope of the off-axis response is not only insignificant, it is also less than the slope of the reflectivity response of the board in the region of increasing on-axis lighting.

Unlike paste or boards, the pads have less of a differentiation between these slope of the off-axis lighting response when compared against the on-axis lighting response.

This recognized different rate of response of paste can be identified and used to detect paste on boards.

In yet another embodiment of the invention, the analyzer 110 examines a rate of change of a single pixel value from a number of images, where each of the different images has a different lighting level changed by the illumination changer 112 prior to the acquiring of each of the different images.

For example, to differentiate paste from board, a rate of change of a pixel representing paste from an image taken under illumination 11 and an image taken under illumination 13, for example, is higher than a rate of change of a pixel representing board from an image taken under illumination 11 and an image acquired under illumination 13. In this example, it is easy to distinguish paste from board.

Differentiating paste from pad can require more than comparing the rate of changes of the images acquired under image illumination 11 and image illumination 13. In an embodiment, after identifying the two pixel positions, (one for paste and one for pad in this example) exhibiting a high rate of change in the off-axis region, the rate of change for the same pixels in the on-axis region is determined. For example, the intensity of the pixels from two different images, such as an image under illumination 3 and a image under illumination 6, are compared. If the rate of change in the on-axis region is approximately the same as the rate of change in the off-axis region, the pixel at that position is deemed to be pad. If, however, the rate of change in the on-axis region is substantially less than the rate of change in the off-axis region, the analyzer deems the pixel at that position to be paste. In an alternate embodiment, it is not necessary to compute a rate of change of a second set of images. Instead, the rate of change between two images under illumination 11 and 13, respectfully is combined with the above-mentioned subtraction method. For example, a pixel is deemed to represent paste if a magnitude in an off-axis region of one or more images is significantly greater than a magnitude of a corresponding pixel in a on-axis region. Corresponding pixels are deemed to represent pad if the associated magnitudes, between the two images are approximately equal.

This extension of the subtraction technique can be used to discriminate between regions with more precision and can be used in cases where simple subtraction may be ambiguous.

It should be apparent that one or more reflectivity behaviors can be used for a given application. It should further be apparent that either one of the reflectivity behaviors can overrule the other for indeterminate cases, where the decision depends on the application.

It should be apparent that lighting states can be any combination of off-axis and on-axis lighting in each image. Zero against an increasing intensity was used herein, as an example.

Figure 7:
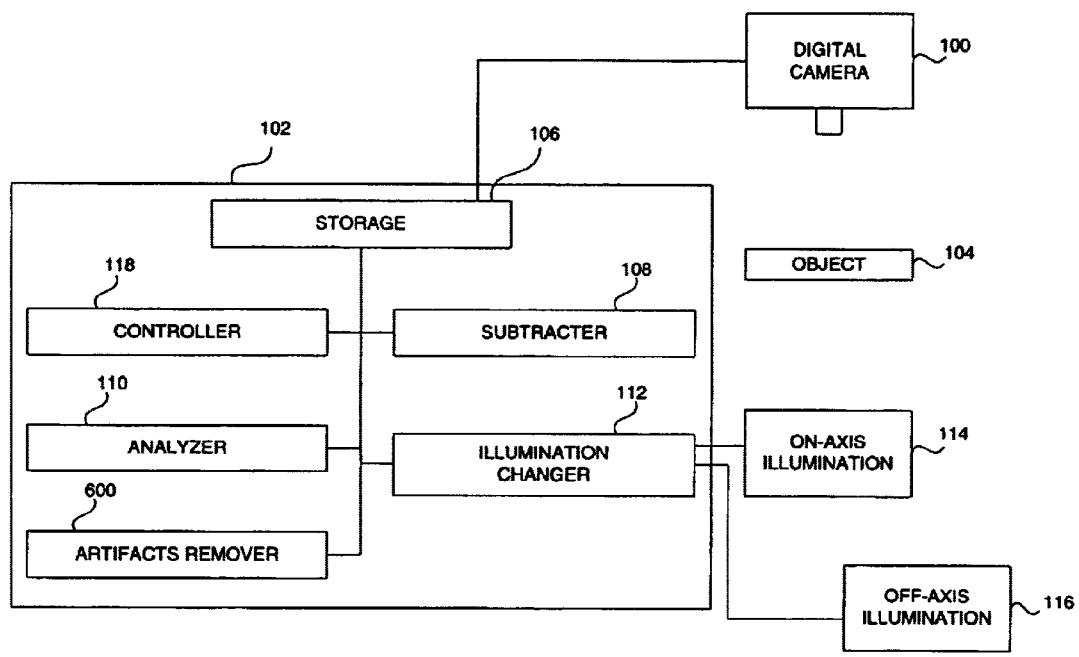
FIG. 7 shows an embodiment of the invention having an artifacts remover.

Improvements to the apparatus include an artifacts remover 600, shown in FIG. 7, for removing artifacts that are caused by 3D relief of pad edges and circuit traces. An output of a difference image can be used to classify pixels as representing paste and as not representing paste. Thus, making the image primarily a binary image. The artifacts above can appear as single pixel chains and can be falsely detected as paste in the above image. Image processing, namely grey scale or binary morphology can be used to remove these artifacts. This technique is well-known in the art.

Figure 3:
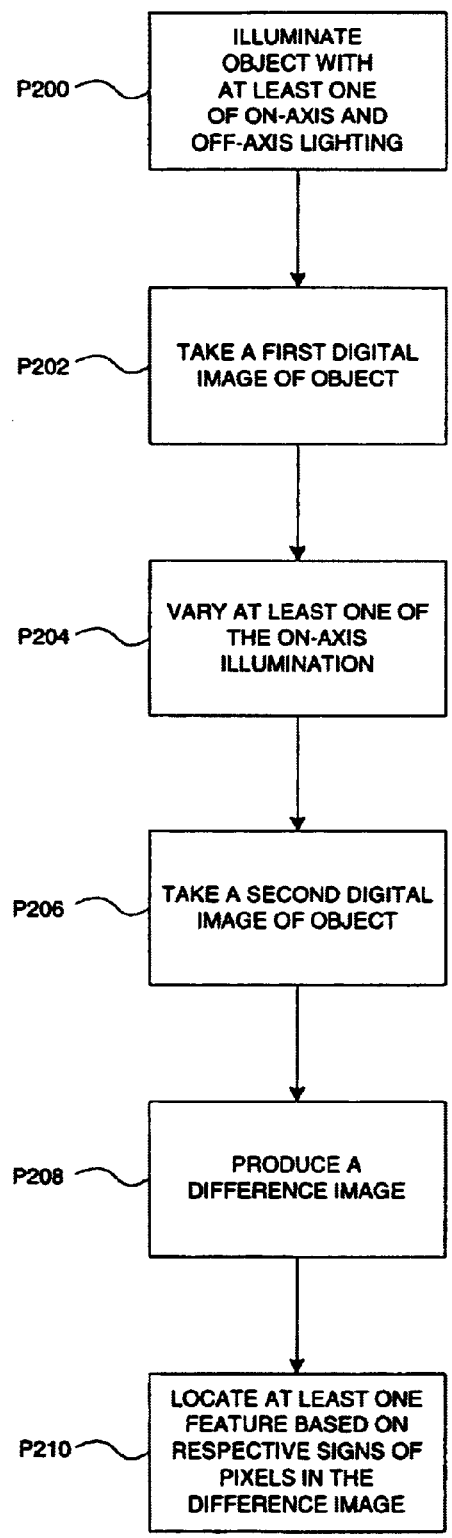
FIG. 3 is a flow chart showing the processing in a first embodiment of the invention.

FIG. 3 is a flow chart which explains the processing in an embodiment of the invention. At P200, an object, for example a circuit board, is illuminated with at least one of on-axis lighting 114 and off-axis lighting 116.

At P202, a first digital image of the object 104 is obtained by digital camera 100 and stored in storage 106.

At P204, the controller 118 instructs the illuminator changer 112 to vary the lighting by changing an intensity of at least one of the on-axis lighting 114 and off-axis lighting 116.

At P206, a second digital image of the object is acquired by the digital camera 100 and stored in storage 106 without moving a digital camera 100 or the object 104 from a position used to obtain the previous digital image.

At P208, the controller 118 instructs the subtracter 108 to produce a difference image by subtracting one of the digital images from another and storing the difference image in storage 106.

At P210, the controller 118 instructs the analyzer 110 to locate at least one feature, for example, solder paste, based on respective signs of grey levels of respective pixels in the difference image.

Figure 4:
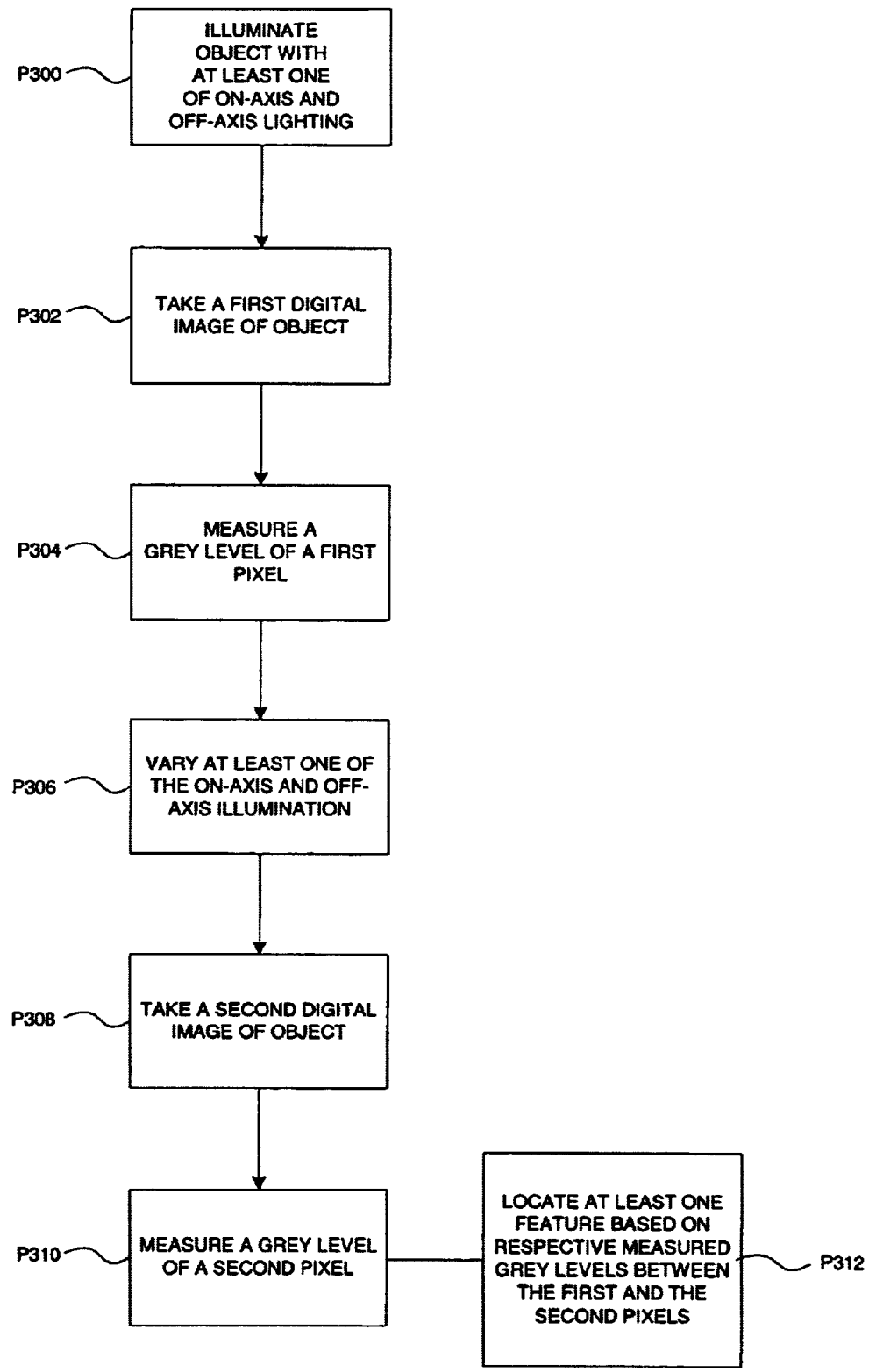
FIG. 4 is a flow chart showing the processing in a second embodiment of the invention.

FIG. 4 shows a flowchart which describes the processing in another embodiment of the invention.

At P300, the controller 118 instructs the illumination changer 112 to illuminate an object 104 with at least one of on-axis lighting 114 and off-axis lighting 116.

At P302, a first digital image of the object 104 is obtained by the digital camera 100 and stored in the storage 106.

At P304, the controller 112 instructs the analyzer 110 to measure a grey level of a first pixel in a portion of the first digital image.

At P306, the controller 118 instructs the illumination changer 112 to vary at least one of the on-axis 114 and the off-axis illumination 116.

At P308, a second digital image of the object 104 is obtained by the digital camera 100 and stored in the storage 106 without moving a position of a digital camera and the object from a position in which they resided during the obtaining of the first digital image.

At P310, the controller 118 instructs the analyzer 110 to measure a grey level of a second pixel in a portion of the second digital image.

At P312, the controller 118 instructs the analyzer 110 to locate at least one feature, for example, solder paste, based on respective measured grey levels between the first and the second pixels.

Figure 5:
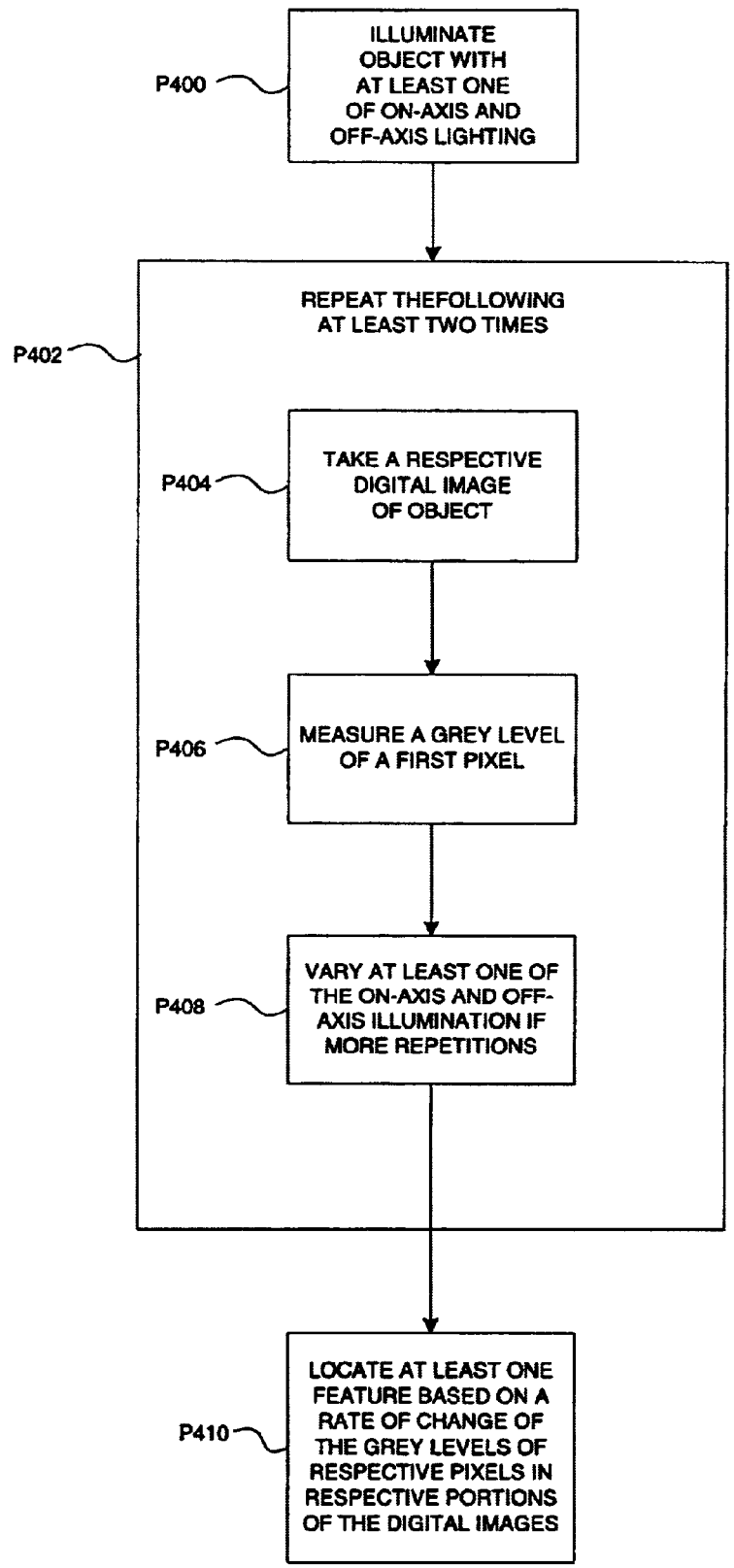
FIG. 5 is a flow chart showing the processing in a third embodiment of the invention.

FIG. 5 shows a flow chart illustrating processing in another embodiment of the invention.

At P400, the controller 118 instructs the illumination changer 112 to illuminate the object 104 with at least one of on-axis lighting 114 and off-axis lighting 116.

P402, shows processes P404 through P408 being repeated at least two times.

At P404, the digital camera 100 acquires a respective digital image of the object 104 and stores the digital image in the storage 106.

At P406, the controller 118 instructs the illumination changer to measure a grey level of a first pixel of the respective digital image.

At P408, the controller instructs the illumination changer 112 to vary at least one of the on-axis 114 and off-axis lighting 116 if more repetitions of processes 404 through 408 are to be performed.

At P410, the controller 118 instructs the analyzer 110 to locate at least one feature, for example, solder paste, based on a rate of change of the grey levels of respective pixels and respective portions of the obtained digital images.

Figure 6:
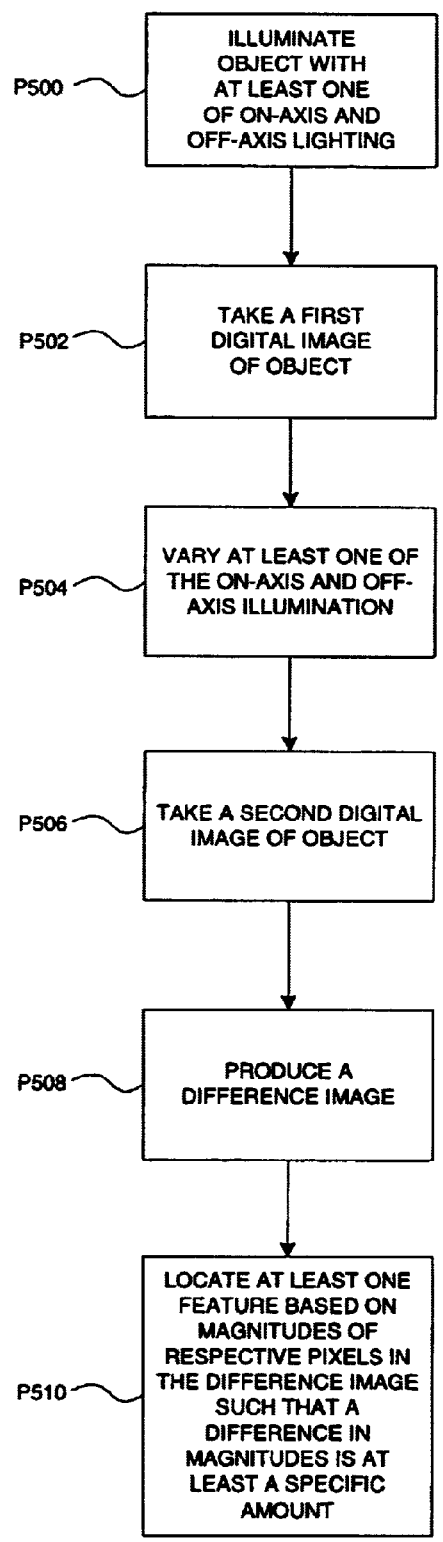
FIG. 6 is a flow chart showing the processing in a fourth embodiment of the invention.

FIG. 6 shows the processing in yet another embodiment of the invention.

At P500, the controller instructs the illumination changer 112 to illuminate the object 104 with at least one of on-axis 114 and off-axis lighting 116.

At P502, a first digital image of the object is obtained by digital camera 100 and the digital image is stored in storage 106.

At P504, the controller 118 instructs the illumination changer 112 to vary an intensity of at least one of the on-axis lighting 114 and the off-axis lighting 116.

At P506, a second digital image of the object 104 is obtained by the digital camera 100 and stored on the storage 106.

At P508, the controller 118 instructs the subtracter 108 to produce a difference image by subtracting one of the first and the second digital image from another of the first and the second digital image. The difference image is stored in the storage 106.

At P510, the controller 118 instructs the analyzer 110 to locate at least one feature, for example, solder paste, based on magnitudes of grey levels of respective pixels in the difference image, such that a difference in magnitude is at least a specific amount.

Each of the just-discussed embodiments can be improved by using an artifact remover 600 during post-processing, shown in FIG. 7. The artifacts remover 600 removes artifacts caused by 3D relief of pad edges, after obtaining each of the digital images in the previous embodiments as shown in FIGS. 3–6. Artifacts remover 600 can remove artifacts, for example, by using morphology.

It should be apparent that the reflectivity properties of other components could be used for identification using the teachings disclosed herein.

Figure 11:
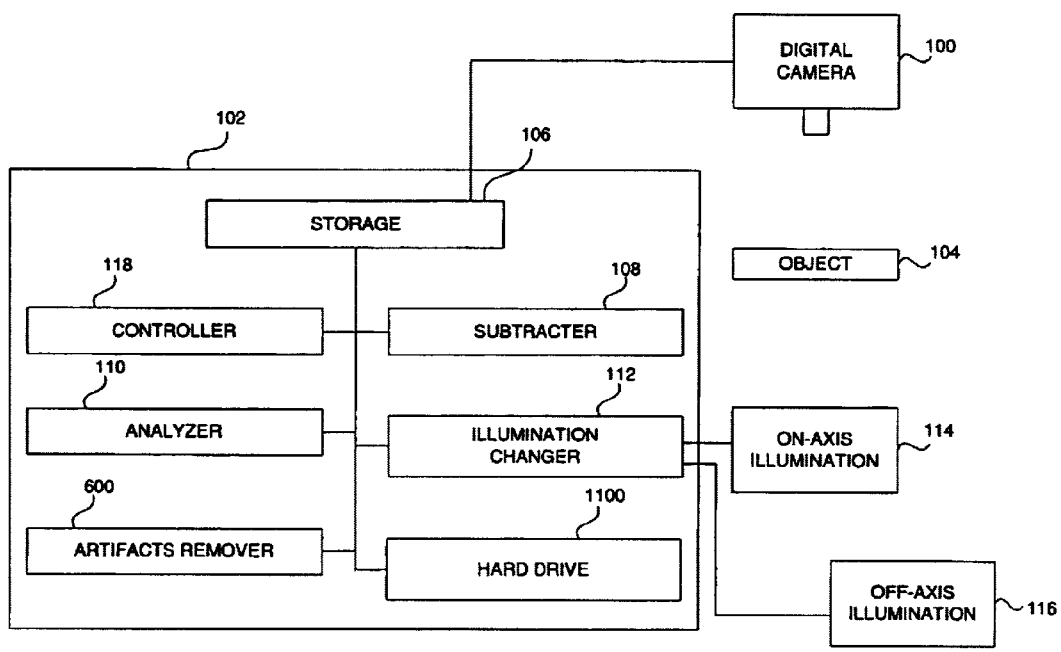
FIG. 11 shows an embodiment of the invention having a hard drive.

The above-mentioned embodiments may be implemented using software, firmware, hardware or any combination of hardware, firmware and software. In addition, software for implementing an embodiment of the invention may be stored on, for example, hard drive 1100, as shown in FIG. 11, floppy disk, CD ROM, DVD, or any other medium capable of storing machine-readable information.

It will be appreciated that although embodiments of the invention described in herein affect inspection of solder paste applied to printed circuit boards, it can be similarly implemented in processes to affect inspection of other materials such as screen printed adhesives, conductive adhesives or the like, applied on substrates other than printed circuit boards. Furthermore, the invention can be implemented and/or the inventive concepts herein modified to be used to inspect solder paste or adhesives applied in-line or applied in other ways. The invention extends to all equivalent structures, mechanisms, acts, and uses, such as are within the scope of the appended claims.

I claim as my invention:

1. An apparatus comprising:

an image processor, said image processor being configured to send a plurality of commands to a digital camera causing the digital camera to obtain a plurality of digital images of an object without moving a location of the digital camera in relation to the object, said image processor being arranged to receive the digital images of the object from the digital camera, and said image processor being configured to control a level of illumination from at least one lighting source for illuminating the object, said image processor comprising:

an illumination changer to change a level of illumination of any of the at least one lighting source, the at least one lighting source illuminating the object, while the position of the at least one lighting source remains the same;

a subtracter to subtract at least a second digital image of the object from a first digital image of the object to produce a difference image of the object, the illumination changer changing a level of illumination of the object before said image processor sends a command to the digital camera to obtain the second digital image;

an analyzer to analyze the difference image and to locate at least one feature of the object based on the difference image; and a controller to control and coordinate the illumination changer, the subtracter, and the analyzer.

2. The apparatus of claim 1, wherein said analyzer locates the at least one feature based on respective signs of pixels in the difference image.

3. The apparatus of claim 1, wherein the at least one lighting source comprises at least one of on-axis illumination and off-axis illumination.

4. The apparatus of claim 3, wherein the illumination changer is arranged to vary a respective intensity of at least one of the on-axis illumination and the off-axis illumination.

5. The apparatus of claim 1, wherein the object includes a circuit board and the at least one feature includes solder paste.

6. An apparatus comprising:

an image processor, said image processor being configured to send a plurality of commands to a digital camera causing the digital camera to obtain a plurality of digital images of an object without moving a location of the digital camera and the object, said image processor being arranged to receive the digital images of the object from the digital camera, and said image processor being configured to control a level of illumination from at least one lighting source for illuminating the object, said image processor comprising:

an illumination changer to change a level of illumination of any of the at least one lighting source, the at least one lighting source illuminating the object, while the position of the at least one lighting source remains the same the illumination changer changing a level of illumination of the object before said image processor sends a command to the digital camera to obtain a next digital image;

an analyzer to analyze a first digital image and a second digital image and to locate at least one feature of the object based on a difference in respective measured grey levels between a first pixel of the first digital image and a second pixel of the second digital image; and a controller to control and coordinate the illumination changer and the analyzer.

7. The apparatus of claim 6, wherein the at least one lighting source comprises at least one of on-axis illumination and off-axis illumination.

8. The apparatus of claim 7, wherein the illumination changer is arranged to vary a respective intensity of at least one of the on-axis illumination and the off-axis illumination.

9. An apparatus comprising:

an image processor, said image processor being configured to send a plurality of commands to a digital camera causing the digital camera to obtain a plurality of digital images of an object without moving a location of the digital camera and the object, said image processor being arranged to receive the digital images of the object from the digital camera, and said image processor being configured to control a level of illumination from at least one lighting source for illuminating the object, said image processor comprising:

an illumination changer to change a level of illumination of any of the at least one lighting source, the at least one lighting source illuminating the object, while the position of the at least one lighting source remains the same the illumination changer changing a level of illumination of the object before said image processor sends a command to the digital camera to obtain a next digital image;

an analyzer to analyze the plurality of digital images and to locate at least one feature of the object based a rate of change of grey levels of respective pixels in respective portions of the digital images; and a controller to control and coordinate the illumination changer and the analyzer.

10. The apparatus of claim 9, wherein the at least one lighting source comprises at least one of on-axis illumination and off-axis illumination.

11. The apparatus of claim 10, wherein the illumination changer is arranged to vary a respective intensity of at least one of the on-axis illumination and the off-axis illumination.

12. The apparatus of claim 9, wherein the object includes a circuit board and the at least one feature includes solder paste.

13. The apparatus of claim 1, wherein the analyzer is arranged to locate the at least one feature based on magnitudes of respective pixels of one of the first digital image and the second digital image being at least a specific amount greater than respective pixels of another of the first digital image and the second digital image.

14. The apparatus of claim 1, further comprising:

an artifacts remover to remove artifacts in the difference image, the artifacts being caused by 3D relief of edges of items on the object.

15. The apparatus of claim 6, further comprising:

an artifacts remover to remove artifacts in the difference image, the artifacts being caused by 3D relief of edges of items on the object.

16. The apparatus of claim 9, further comprising:

an artifacts remover to remove artifacts in the difference image, the artifacts being caused by 3D relief of edges of items on the object.

17. A machine-readable medium having information recorded thereon, such that when the information is read into an image processor, the image processor is caused to:

illuminate an object at a level of illumination with a lighting source;

take a first digital image of the object with a digital camera;

vary the level of illumination of the object, while the position of the lighting source remains the same;

take a second digital image of the object with the digital camera while the digital camera and the object are in a same position as the digital camera and the object when the first digital image of the object was taken;

subtract one of the first and the second digital image from another of the first and the second digital image to produce a difference image; and locate at least one feature of the object based on the difference image.

18. The medium of claim 17, wherein when the image processor is caused to locate the at least one feature of the object, the image processor locates the at least one feature based on respective signs of pixels in the difference image.

19. The medium of claim 17, wherein when the image processor is caused to illuminate the object, the image processor causes the object to be illuminated by using at least one of on-axis illumination and off-axis illumination.

20. The medium of claim 19, wherein when the image processor varies the illumination, the image processor causes a respective intensity of at least one of the on-axis illumination and the off-axis illumination to vary.

21. The medium of claim 17, wherein the object includes a circuit board and the at least one feature includes solder paste.

22. A machine-readable medium having information recorded thereon such that when the information is read into an image processor, the image processor is caused to:

illuminate an object at a level of illumination, with lighting source;

take a first digital image of the object with a digital camera;

vary the level of illumination of the object, while the position of the lighting source remains the same;

take a second digital image of the object while the digital camera and the object are in a same position as the digital camera and the object when the first digital image of the object was taken; and locate at least one feature of the object based on a difference in respective measured grey levels of a first pixel representing a portion of the first digital image and a second pixel representing a portion of the second digital image.

23. The medium of claim 22, wherein when the image processor is caused to illuminate the object, the image processor causes the object to be illuminated by using at least one of on-axis illumination and off-axis illumination.

24. The medium of claim 23, wherein when the image processor varies the illumination, the image processor causes a respective intensity of at least one of the on-axis illumination and the off-axis illumination to vary.

25. A machine-readable medium having information recorded thereon such that when the information is read into an image processor, the image processor is caused to:

illuminate an object at a level of illumination, with a lighting source;

repeat the following at least two times:

take a respective digital image of the object while a digital camera and the object are kept in a same position, and vary the level of illumination of the object, while the position of the lighting source remains the same when another repetition is to be performed;

locate at least one feature of the object based on a rate of change of grey levels of respective pixels in respective portions of the digital images.

26. The medium of claim 25, wherein when the image processor is caused to illuminate the object, the image processor causes the object to be illuminated by using at least one of on-axis illumination and off-axis illumination.

27. The medium of claim 26, wherein when the image processor varies the illumination, the image processor causes a respective intensity of at least one of the on-axis illumination and the off-axis illumination to vary.

28. The medium of claim 25, wherein the object includes a circuit board and the at least one feature includes solder paste.

29. The medium of claim 17, wherein when the image processor locates the at least one feature, the image processor locates the at least one feature based on magnitudes of respective pixels of one of the first digital image and the second digital image being at least a specific amount greater than respective pixels of another of the first digital image and the second digital image.

30. The medium of claim 17, wherein the image processor is further caused to remove artifacts caused by 3D relief of edges of items on the object.

31. The medium of claim 22, wherein the image processor is further caused to remove artifacts caused by 3D relief of edges of items on the object.

32. The medium of claim 25, wherein the image processor is further caused to remove artifacts caused by 3D relief of edges of items on the object.

* * * * *